US010197576B2

(12) United States Patent
Suckau et al.

(10) Patent No.: US 10,197,576 B2
(45) Date of Patent: Feb. 5, 2019

(54) MASS SPECTROMETRY IMAGING WITH SUBSTANCE IDENTIFICATION

(76) Inventors: Detlev Suckau, Grasberg (DE); Martin Schürenberg, Tarmstedt (DE); Rainer Paape, Martfeld (DE); Christine Lübbert, Berlin (DE)

( * ) Notice: Subject to any disclaimer, the term of this patent is extended or adjusted under 35 U.S.C. 154(b) by 785 days.

(21) Appl. No.: 13/291,159

(22) Filed: Nov. 8, 2011

(65) Prior Publication Data

US 2012/0129201 A1 May 24, 2012

(30) Foreign Application Priority Data

Nov. 18, 2010 (DE) .......................... 10 2010 051 810

(51) Int. Cl.
| | | |
|---|---|---|
| G01N 30/72 | (2006.01) | |
| G01N 33/68 | (2006.01) | |
| G01N 23/2258 | (2018.01) | |
| A61K 38/00 | (2006.01) | |

(52) U.S. Cl.
CPC ..... *G01N 33/6848* (2013.01); *G01N 2400/00* (2013.01)

(58) Field of Classification Search
CPC .................................................. G01N 33/6848
See application file for complete search history.

(56) References Cited

U.S. PATENT DOCUMENTS

| | | | |
|---|---|---|---|
| 5,808,300 A | 9/1998 | Caprioli | |
| 6,188,064 B1 | 2/2001 | Koster | |
| 7,070,949 B2 * | 7/2006 | Suckau et al. | 435/23 |
| 7,667,196 B2 | 2/2010 | Schurenberg | |
| 7,873,478 B2 | 1/2011 | Suckau | |
| 2002/0192735 A1 * | 12/2002 | Covey et al. | 435/23 |
| 2003/0203483 A1 * | 10/2003 | Seshi | 435/366 |
| 2006/0063145 A1 | 3/2006 | Suckau | |
| 2007/0069122 A1 | 3/2007 | Augustin et al. | |
| 2007/0090285 A1 * | 4/2007 | Whitney et al. | 250/281 |
| 2007/0114375 A1 | 5/2007 | Pevsner et al. | |
| 2008/0142703 A1 | 6/2008 | Schurenberg | |
| 2009/0039282 A1 * | 2/2009 | Haase et al. | 250/423 R |
| 2009/0215069 A1 * | 8/2009 | Christ et al. | 435/7.1 |
| 2011/0280455 A1 | 11/2011 | Alexandrov | |
| 2013/0338933 A1 * | 12/2013 | Deciu et al. | 702/20 |
| 2014/0142180 A1 * | 5/2014 | Birsoy et al. | 514/557 |

FOREIGN PATENT DOCUMENTS

GB 2478398 A 9/2011

OTHER PUBLICATIONS

Herring et al. (2007) Direct tissue analysis by matrix-assisted laser desorption ionization mass spectrometry: application to kidney biology, Semin Nephrol., vol. 27, No. 6, pp. 597-608.*
Crobu, Salvatore (2009) "Analisi comparativa dei metaboliti presenti nelle urine di soggetti sani ed affetti da carcinoma alla vescica mediante", Doctoral Thesis,, pp. 1-33. See also http://www.univr.it/main?ent=catalogoaol&id=337595&page=dettaglioPubblicazione&lang=en.*
Wong et al. (2009) Comparison of Different Signal Thresholds on Data Dependent Sampling in Orbitrap and LTQ Mass Spectrometry for the Identification of Peptides and Proteins in Complex Mixtures, J. Am. Soc. Mass. Spectrom., vol. 18, No. 8, pp. 1405-1414.*
Demeure et al. (2007) Rational Selection of the Optimum MALDI Matrix for Top-Down Proteomics by In-Source Decay, Anal. Chem., vol. 79, No. 22, pp. 8678-8685.*
Cazares, L. H. et al, "Spectrometry of a Specific Fragment of G01N33/68 Mitogen-Activated Protein H01J49/00Kinase/Extracellular Signal-Regulated Kinase Kinase Kinase 2 Discriminates Cancer from Uninvolved Prostate Tissue", Clinical Cancer Research, vol. 15, No. 17, Sep. 1, 2009 (Sep. 1, 2009), pp. 5541-5551.
EP Search Report dated Mar. 2, 2012.
Luxembourg S.F., Mize T.F., McDonnell L. A. and Heeren R.M.A, "High-Spatial Resolution Mass Spectrometric Imaging of Peptide and Protein Distributions on a Surface", Analytical Chemistry, v. 76, pp. 5339-5344 (2004).
Debois D., Bertrand V., Quinton L., De Pauw-Gillet M. and De Pauw E., "MALDI-In Source Decay Applied to Mass Spectrometry Imaging: A New Tool for Protein Identification", Analytical Chemistry v. 82, pp. 4036-4045 (2010).

* cited by examiner

*Primary Examiner* — Manjunath N Rao
*Assistant Examiner* — Samuel W Liu
(74) *Attorney, Agent, or Firm* — Benoit & Côté Inc.

(57) ABSTRACT

A method for the identification and localization of proteins or other biomolecules of a histologic tissue section comprises enzymatically digesting the biomolecules of two similar tissue sections while substantially preserving the biomolecule positions in the tissue sections. Next, a mass spectrometric image of the digest products in one of the tissue sections is acquired. Then, the digest products of the other tissue section are extracted and separated and the mass spectra and daughter ion spectra of all the digest products are acquired. A list of all identifiable biomolecules of the tissue section is created by comparing the mass spectra and daughter ion spectra with spectra in biomolecule structure databases or spectral libraries. Finally, the biomolecules in the list are assigned to digest products of the same mass in the mass spectra used to create the mass spectrometric image of the thin tissue section.

17 Claims, 3 Drawing Sheets

MASS SPECTROMETRY IMAGING WITH SUBSTANCE IDENTIFICATION

BACKGROUND

The invention relates to mass spectrometry imaging of histologic thin tissue sections. The term "mass spectrometric image" of a thin tissue section which is obtained by mass spectrometry imaging (MSI) is defined here as an image which contains a mass spectrum with molecular information for every image point. The "mass spectrometric image" thus corresponds precisely to term "color image" which contains a color spectrum for every image point. The color spectrum contains the complete color information of the visible light spectrum, even if our eye summarizes the color spectrum into a single color impression. And just as it is possible to generate images of selected colors from a color image, for example red, yellow and blue images for a color print, it is possible to use a mass spectrometric image to generate "mass-selective images", each of which displays the concentration of a molecular ion in its spatial distribution across the thin tissue section. Images which are derived from several selective images, and which can be used to spatially characterize the tissue states, are also of interest.

Histology is the science of human, animal and plant tissues, in particular of their structure and function. A histologic classification is generally carried out on a stained thin tissue section a few micrometers thick, and concerns the cell types present, the organ-specific differentiation of the tissue, bacterial and parasitic pathogens in the tissue, the disease states of the tissue and distributions of pharmaceutical products or their metabolites. The classification can be limited to one or more sub-areas of a tissue section or even apply to only one or more individual cells or organelles. The disease states of human tissue may relate to inflammatory diseases, metabolic diseases and the detection of tumors, especially the differentiation between benign and malignant forms of tumor or the prognosis of therapeutic success and survival expectation of a patient.

The generation of histologic tissue sections for an optical analysis involves the following steps: (a) the tissue is stabilized by deep freezing or chemical fixation, e.g. with formalin. (b) a thin section around 10 micrometers thick is cut with a microtome and (c) the tissue section is fixed, e.g. on a microscope slide, and stained.

Tissue stabilization means that the tissue structures, the cells of the tissue themselves and even intracellular structures (organelles such as the cell nucleus, endoplasmic reticulum, and mitochondria) are preserved in the tissue section. Usually, tissue stabilization is performed by deep-freezing. A well-known chemical tissue stabilization is termed "formalin-fixed paraffin-embedded" (FFPE); whereby the proteins within the tissue are cross-linked by reaction with formalin. Clinical archives hold millions of tissue samples, collected for more than a hundred years, stabilized by FFPE or similar methods. In routine histologic analyses, the structures of the tissue section are imaged with the aid of optical microscopes or with a "slide scanner". A visual image of the tissue section recorded in this way can have a spatial resolution of about 250 nanometers.

The state of a tissue in relation to disease or infection with pathogens as compared to a healthy tissue sample can become apparent by a characteristic composition of substances. Usually, the substances are measured mass spectrometrically without imaging from homogenized pieces of tissue. The tissue state can be characterized by molecular information, in detail by the concentrations of different substances in relation to each other. If the substances are soluble and their concentrations sufficiently high, their concentrations can be detected by mass spectrometric analysis. The substances can be all types of biological substances, e.g. proteins, nucleic acids, lipids, polysaccharides or conjugates like glycoproteins or glycolipids. An unusual pattern can result when certain biological substances are modified, underexpressed or overexpressed. Proteins, in particular, can be modified in characteristic ways, e.g. by posttranslational modifications (PTM) or controlled degradation of the protein chain.

Mass spectrometry with ionization of the samples by matrix-assisted laser desorption and ionization (MALDI) has been used successfully for many years for the determination of molecular masses, and for the identification of biological substances, particularly proteins and peptides. This type of analytical technique can also be used for complex mixtures with some success. For example, methods of mathematical statistics can be used to mass spectrometrically determine the state of a tissue sample. Before these methods are used, a large number of tissue samples of different classifications (so-called "cohorts") have to be provided, e.g. for the adjustment or learning of parameters. The sample formats can be homogenates of pieces of tissue or extracts.

In imaging mass spectrometric analysis, i.e. the acquisition of a mass spectrometric image, tissue sections are mass spectrometrically analyzed, usually with ionization by matrix-assisted laser desorption (MALDI). To this end, a thin-tissue section is placed onto an electrically conductive microscope slide as sample support. A thin layer of a matrix substance is then applied onto the tissue section by a suitable method not generating much lateral mixing of the tissue components, in such a way that finally the dried matrix substance layer contains the soluble peptides (and also other soluble substances) in an extracted form. The sample support is introduced into a mass spectrometer, and mass spectra of the individual image points are acquired.

The raster scan method according to Caprioli (U.S. Pat. No. 5,808,300 A) is predominantly used for the imaging mass spectrometric analysis; however, it is also possible to acquire a stigmatic image of a region of the tissue sample (Luxembourg et al., Analytical Chemistry, 76(18), 2004, 5339-5344: "High-Spatial Resolution Mass Spectrometric Imaging of Peptide and Protein Distributions on a Surface").

In both cases, a "mass spectrometric image" of the tissue section is obtained, where for every image point the molecular information is present in the form of a mass spectrum. As is usual for MALDI, every mass spectrum is summed from a large number of individual spectra and covers an appropriate mass range, which can extend from around 100 to 60,000 atomic mass units. The region below 800 atomic mass units is measured to determine lipid distribution and the distribution of pharmaceutical products and their metabolites. The range between 800 and 60,000 atomic mass units is measured to determine the distribution of endogenous peptides and soluble proteins.

Various suitable methods for the preparation of tissue sections for mass spectrometry imaging analysis are known from the documents DE 10 2006 019 530 B4 and DE 10 2006 059 695 B3 (M. Schurenberg et al.; 2006). The matrix solution can be applied to the tissue section by pneumatic spraying, nebulizing by vibration, or by nanospotting of droplets, for example. It is no trivial task to apply the matrix solution because, firstly, a strong lateral diffusion of the biological substances must be avoided, secondly, the soluble biological substances must be extracted from the tissue section as completely as possible and incorporated into the crystals of the matrix layer, and thirdly, a favorable ratio of biologically relevant substances to impurities must be achieved. Some impurities greatly reduce the ionization yield. The kind of application of the matrix substance to the thin tissue section, the limitations for the spot diameter of the laser beam on the specimen, and also the quantities of substance required for the laser desorption mean that mass spectrometric images of tissue sections are currently limited to a spatial resolution of around 20 micrometers.

If the mass spectrometric images are acquired with a relatively coarse grid of 50 micrometers, this already produces 240,000 mass spectra for an area of 20 by 30 millimeters. Each time-of-flight mass spectrum can, in turn, comprise around 30,000 ion current measurement values or more. As is usual for MALDI, a hundred or more individual time-of-flight spectra are acquired and summed for each mass spectrum. Even in modern mass spectrometers with a high laser pulse rate, the acquisition of a mass spectrometric image takes many hours or even days depending on the size of the thin section and the width of the scanning raster selected.

One of the advantages of ionization by matrix-assisted laser desorption is that practically only singly charged ions of unfragmented analyte substance molecules are produced. It is therefore relatively easy to interpret the mass spectra. The mass spectra of the individual image points each show usually the mass signals of 20 to 400 soluble endogenous peptides in the mass range between 800 and 5,000 atomic mass units. The signals of the peptides emerge from a broad chemical background. Lighter proteins with less than around 5,000 atomic mass units are usually called peptides.

When MALDI time-of-flight mass spectrometers are used for imaging, a mass accuracy of around 50 millionths of the mass (50 ppm) can be achieved in the mass spectra of the image. If MALDI is used with other mass spectrometers, for example ion cyclotron resonance mass spectrometers or time-of-flight mass spectrometers with orthogonal ion injection, even better mass accuracies can be achieved.

"Monoisotopic ions" are defined as those ions from an isotopic group which are composed only of $^1H$, $^{12}C$, $^{14}N$, $^{16}O$, $^{31}P$, and $^{32}S$ and contain no other isotopes of these elements. The monoisotopic ions are always the lightest ions of the isotopic group, which also contains ions with admixtures of other isotopes such as $^2H$, $^{13}C$, $^{15}N$, $^{17}O$, $^{18}O$, and $^{34}S$.

If peptides with molecular weights in the range between 1,000 and 5,000 atomic mass units are used for the imaging at correspondingly high mass resolution, a well-resolved isotopic group comprising several individual mass signals appears in the mass spectra of the thin-section image for every peptide. As is usual in mass spectrometry, individual mass signals of an isotopic group can immediately be summarized in the monoisotopic mass by known methods and entered in a table which corresponds to a reduced mass spectrum. It is possible to use either the monoisotopic molecular mass or the monoisotopic ion mass, which differ by the mass of one proton in the case of ionizations by MALDI. The document DE 198 03 309 C1 (C. Koster, GB 2 333 893 B; U.S. Pat. No. 6,188,064 B1, 1998) describes in detail a preferred method for the determination of the ion masses, and particularly the mass of the monoisotopic ions, which has become well known under the term "SNAP". This method is also capable of recognizing the overlapping of isotopic groups of several peptides which differ by one or more mass units.

When the term "monoisotopic mass" is used below, it can mean either the molecular mass, i.e. the mass of the neutral molecule, or the ion mass, i.e. the mass of the protonated molecule.

The term "mass-selective image" designates an image of the tissue section which shows only the intensity distribution of the ions of this mass of a peptide, usually a monoisotopic ion mass. These images of selected masses are usually very noisy. Special types of smoothing process (see patent application DE 10 2010 009 853, for example) can be used to produce low-noise images which are very impressive and informative.

Mass spectrometry imaging is already eminently suited for classifying tissue sections according to tissue states, such as tumorous developments, and the visual representation of the tissue states. See for this the document DE 10 2004 037512 A1 (D. Suckau et al.; GB 2 418 773 B; US 2006/0063145 A1; 2004). These images are also good for measuring the distribution of pharmaceutical products of sufficient molecular dimension and their metabolites in the tissue, because the molecular weight of the pharmaceutical products and their metabolites are known and they can therefore be easily identified.

So far, however, it has only been possible in exceptional cases, and with laborious methods, to identify some of the peptides and proteins involved from such mass spectra of individual image points from thin sections, and to show, in particular, the distribution of these peptides in the thin section (see for example L. H. Cazares: "Imaging Mass Spectrometry of a Specific Fragment of Mitogen-Activated Protein Kinase/Extracellular Signal-Regulated Kinase Kinase Kinase 2 Discriminates", Clin Cancer Res (17), 15; 2009). The identification is of particular interest in the search for biomarkers for certain tissue states, such as cancerous tumors.

In mass spectrometry imaging, a direct identification of endogenous peptides and proteins from the thin section is so far only possible in rare cases; an identification therefore requires additional measures. In non-imaging mass spectrometry, these measures usually entail a fragmentation of the proteins or their ions to increase the information content, whether fragmentations of the protein molecules by enzymatic digest, or fragmentations of selected parent ions for the generation of daughter ions, or even combinations of both. Proteolytic peptides, measurable between 800 and 4,000 atomic mass units, are peptides which result from the enzymatic degradation of the protein chain, e.g. by digestion with the protease trypsin. Large portions of the amino acid sequence can be read from daughter ion mass spectra; this makes an identification of these proteins possible. The methods for acquiring daughter ion mass spectra consume, however, considerable quantities of substance; for mass spectrometric imaging, the amount of substance of an image point is hardly sufficient for a daughter ion spectrum acquisition. Up to now, attempts at generating daughter ion spectra showed that daughter ion spectra of moderate quality only can be obtained from one or sometimes two high-intensity peptides of an image point (see for example D. Debois et al, "MALDI-In Source Decay Applied to Mass Spectrometry Imaging: A New Tool for Protein Identification", Analytical Chemistry, Vol. 82, 4036-45; 2009), but this is by no means sufficient for a substance identification on a larger scale.

For non-imaging MALDI mass spectrometry on individual samples it is known that the identification of proteins is particularly successful via an enzymatic, for example tryptic, digestion of the proteins in conjunction with precise mass determination of the digest peptides or acquisition of their daughter ion spectra. An excellent measurement method, known by the term "LC-MALDI" (an abbreviation for "liquid chromatography matrix-assisted laser desorption and ionization), combines a separation of the digest peptides by liquid chromatography (HPLC), preparation of MALDI samples for separated fractions and acquisition of MALDI mass spectra and daughter ion spectra by a MALDI time-of-flight mass spectrometer (see U.S. Pat. No. 7,070,949 B2; D. Suckau et al.; 2001; equivalent to GB 2 387 653 B and DE 101 58 860 B4). On the basis of the precise masses of the digest peptides and their daughter ion spectra, computer programs can be used to select proteins from large protein databases which would lead to these digest peptides and their daughter ion spectra, given known digestion and fragmentation schemes. The protein databases usually contain the sequences of the amino acids; but it is also possible to use DNA information to identify the proteins ("open reading frames").

Some research groups have therefore already attempted to enzymatically digest the proteins of a thin tissue section in situ for a better identification of individual proteins with the aid of the digest peptides. However, this digestion leads to a strong lateral diffusion of the digest peptides, and thus to an image with far less spatial resolution. In addition, the diffusion causes a strong dilution if the digested protein was localized in a small spot only, which puts many digest peptides below the detection limit.

But even if a digestion were successful with conservation of the protein positions, one would still not have achieved the goal. Since the thin tissue sections contain complex mixtures of proteins, an extremely high mass accuracy would be required for identification. A short example might explain this: for a species whose thin section is investigated, there can easily be 50,000 known proteins in the database, and digestion of these proteins would produce millions of digest peptides. If only around half of these digest peptides, let us say half a million, fell into the favorable mass range from 800 to 4,000 atomic mass units, the digest peptide of a certain monoisotopic mass number could be one of, on average, around 150 digest peptides which could occur per atomic mass unit in the mass range between 800 and 4,000 atomic mass units. The masses of these 150 digest peptides are also relatively close together; they each have a roughly Gaussian distribution with a full width at half-maximum of around 0.25 atomic mass units. The digest peptides of the thin section could only rarely be distinguished from each other, even with maximum mass resolution and maximum mass accuracy.

Therefore, the prior art direct mass spectrometric imaging methods essentially only detect and analyze the endogenous peptides and some soluble light proteins. There is no access to the most interesting non-soluble, large or immobilized biomolecules, whether the biomolecules are immobilized by chemical preparation or by the natural structure within cells. In FFPE samples with completely cross-linked peptides and proteins, not even the endogenous peptides can be analyzed. However, if, the biomolecules of the tissue section are in situ enzymatically digested, the vast and complex mixture of digest products in each image point and the limited mass accuracy does not allow the identification of the biomolecules by the usual identification procedures.

SUMMARY

In accordance with the principles of the invention, a method for the identification and localization of proteins of a histologic thin tissue section, comprises the following steps:

a) the proteins of two tissue sections are in situ enzymatically digested with exactly the same digestion method and with utmost conservation of their position, the two tissue sections being nearby cuts from the same tissue sample;

b) a mass spectrometric image of the digest peptides in the first thin tissue section is acquired;

c) digest peptides are extracted from the second tissue section, separated by a chromatographic or electrophoretic separation method and investigated by a mass spectrometer, which acquires mass spectra and daughter ion mass spectra of all accessible digest peptides, if possible with the same ionization method as used for obtaining the mass spectrometric image in step (b);

d) the proteins of the tissue are identified by comparing the mass spectra and daughter ion mass spectra of the digest peptides of the second tissue section with protein databases or spectral libraries, and a list of the proteins with their digest peptides is created; and e) the proteins in the list are assigned, on the basis of the measured or calculated masses of their digest peptides, to those digest peptides in the mass spectra of the mass spectrometric image of the thin tissue section which have the same mass.

A preferred embodiment uses a MALDI time-of-flight mass spectrometer for step (b) and LC-MALDI on the same mass spectrometer in step (c). The two mass spectrometric acquisition processes of steps (b) and (c) each take hours or even days, depending on the size of the thin section, on the width of the raster scan, the duration of the chromatographic separation and the number of chromatographic fractions. The two processes result in data volumes in magnitude of gigabytes to terabytes. The data from the measurements of step (c) can be used to determine the underlying proteins in the familiar way using protein databases or spectral libraries; there are numerous computer programs available for this task. Around 200 to 1,000 different proteins with several thousand digest peptides are typically identified for a thin tissue section.

The invention intentionally does not use the usual method of homogenizing and digesting a larger peace of the tissue, and to identify the proteins therein. This method presents about the tenfold number of proteins, but most of the proteins do not match with the proteins seen in the mass spectrometric image. The high number of proteins only vastly increases the number of ambiguities in the identification of the proteins in the mass images; this method, therefore, is by no means helpful.

The proteins in this list of proteins and digestion peptides of the second tissue section can now be assigned to the mass spectrometric image of the thin section, either directly or after further intelligent filtering. Since each digest peptide is preferably characterized with its monoisotopic mass in the mass spectra of the image, all that is required is simply to assign all proteins which have a digest peptide of the same monoisotopic mass—within a measurement error range or a predefined tolerance range. There will be ambiguities in the identification, but the ambiguities can be reduced or even eliminated with suitable filters and by visual or computational correlations of the mass-selective digest images of a protein.

The mass-selective images of all digest peptides of a protein which correlate well with each other can be summarized into an image of the protein distribution in each case. These images of the protein distributions can be processed further, for example they can be smoothed with an edge-preserving smoothing process. Eventually a library of the protein-specific images (images with distributions of the individual proteins) in this thin section is available, which allows deep insights into the molecular structure and the function of the tissue and even may show irregularities in the concentration profiles, e.g., by overexpression, underexpression or unusual modifications.

In another embodiment, the method basically used to identify peptides and proteins in mass spectrometric images of tissue sections, can easily be applied to identify more complex biomolecules, as for instance protein-conjugates with polysaccharides or lipids.

DETAILED DESCRIPTION

Figure 5:
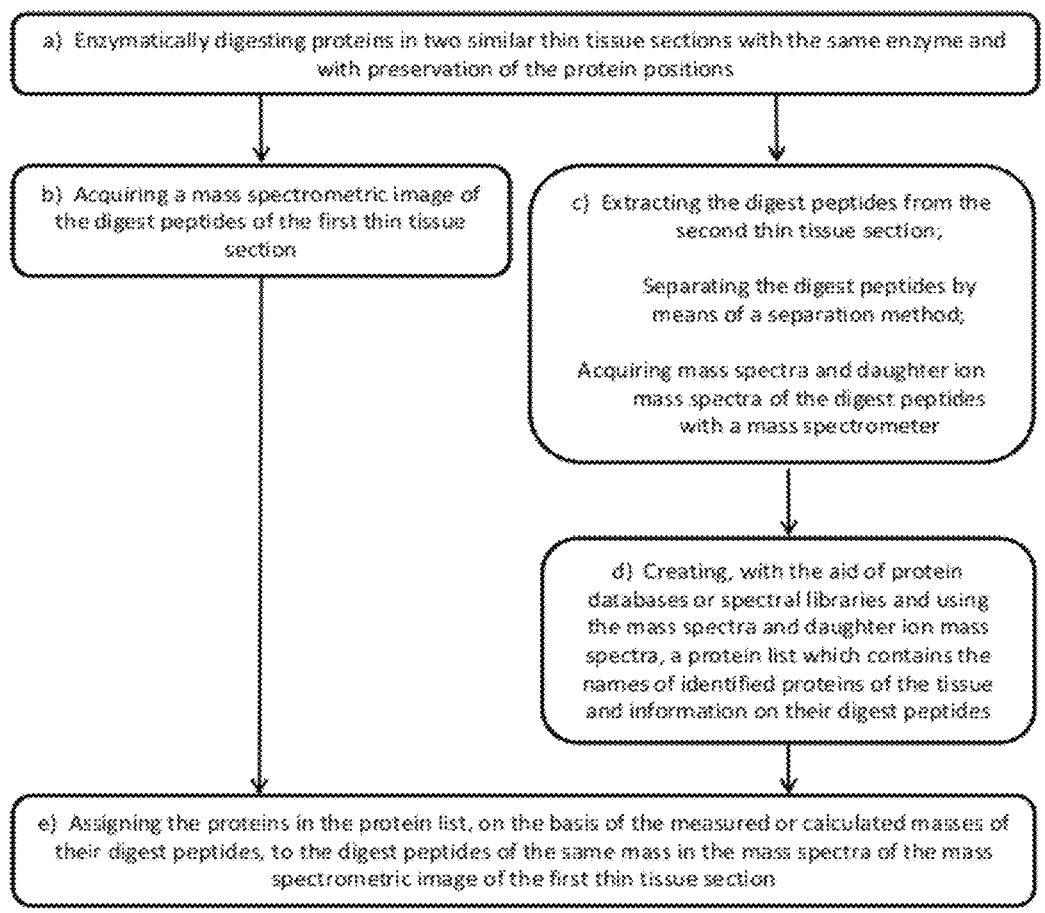
FIG. 5 presents a block diagram of a preferred method.

According to the invention, the identification of spatially distributed proteins in thin tissue sections basically comprises several steps, although not all steps have to be carried out in this order. In step (a), enzymatic digestion of the proteins of two thin tissue sections is achieved with the same type of digestion and with best conservation of the protein positions. In step (b), a spatially well-resolved mass spectrometric image of the digest peptides is acquired from the first tissue section. In a step (c), the digest peptides of the second tissue section are extracted in total without spatial resolution, then separated into fractions, e.g. by chromatographic or electrophoretic methods, and mass spectra and daughter ion mass spectra are acquired from the fractions using a high-resolution tandem mass spectrometer. From these mass and daughter ion spectra, in step (d), a list of several hundred proteins which are present in the tissue can be created, using well-known methods, based on protein databases or spectral libraries. There are many computer programs available for this task. This list of proteins also comprises the digest peptides with their measured or, even better, theoretically calculated monoisotopic masses which can each be assigned to a protein. In step (e), the proteins from this list can then be assigned to the digest peptides with the same monoisotopic masses in the mass spectra of the image of the spatially resolved digest peptides. By using intelligent filtering and confirmation methods, ambiguous assignments can be greatly reduced. The assignment is most easily performed on the basis of the monoisotopic masses of the digest peptides of the proteins. FIG. 5 shows a block diagram of the steps (a) to (e) of this method.

For the enzymatic digestion of the proteins inside the two thin tissue sections with best conservation of the protein positions in step (a) the enzyme, for example trypsin, is applied by spraying an enzymatic solution several times, preferably in a very thin layer, almost dry, onto the dry thin tissue sections. In every spray burst, the droplets of the spray mist should be applied only in quantities that do not overlap on the thin tissue section. The droplets are dried between the spray bursts. When the surface of the thin section is practically completely covered with a thin layer of the enzyme, the spraying is stopped. The dried thin tissue section is now incubated for some hours at the optimum digest temperature, typically for three hours at 37° C. and almost 100% humidity. In the humidity, the thin tissue section absorbs sufficient water to allow a weak diffusion of the enzyme and a digestion of the proteins in the slightly swollen thin section. An extensive digestion is achieved after some hours. The enzyme and peptides will move during this time by diffusion over distances of around ten to twenty micrometers, i.e. far enough for the enzyme to completely penetrate the thin tissue section, but not far enough to essentially affect the spatial resolution.

The digestion is usually performed by the enzyme trypsin, which exists in several slightly different forms. Since it cuts the chain of the amino acids in the proteins at two different locations, after the amino acids lysine and arginine respectively, digest peptides with an average length of ten amino acids result, given complete digestion, albeit with a broad Poisson distribution. Since the digestion is inhibited at a few locations for structural reasons, the distribution of the digest peptides shows a maximum at around 1,500 atomic mass units (instead of 1,200 atomic mass units for a complete digestion). If the focus of interest is on the proteins, it has proved advantageous to remove the endogenous peptides of the thin tissue section by rinsing before the digestion is performed, in order to subsequently measure only digest peptides of the proteins for the mass spectrometric image. The specialist in the field knows how a peptide-extracting matrix layer can be applied and a mass spectrometric image of the digest peptides can be acquired. The layer of matrix substance can preferably be applied with the same spray apparatus that was used to apply the droplets of enzyme solution. Also the acquisition technique with ionization by matrix-assisted laser desorption in MALDI time-of-flight mass spectrometers, and also in other types of mass spectrometer, is widely known. These procedures allow obtaining a mass image of the digest peptides which is well-resolved in terms of spatial locations and masses.

Figure 3:
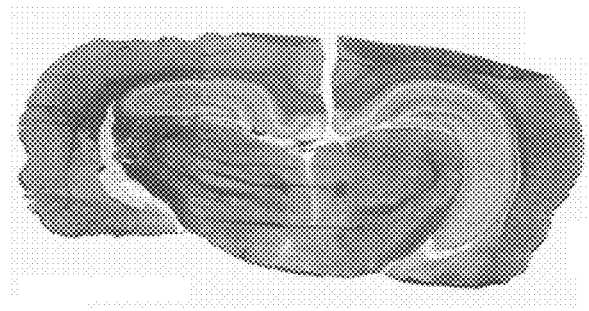
FIG. 3 shows a microscopically obtained image of a thin section of a rat's brain. The left side of this thin section was subsequently covered, and the right side digested by nebulization with trypsin. The whole thin section was then coated with a matrix before a mass spectrometric image was acquired, image point by image point, with a raster scanning method.
Figure 4:
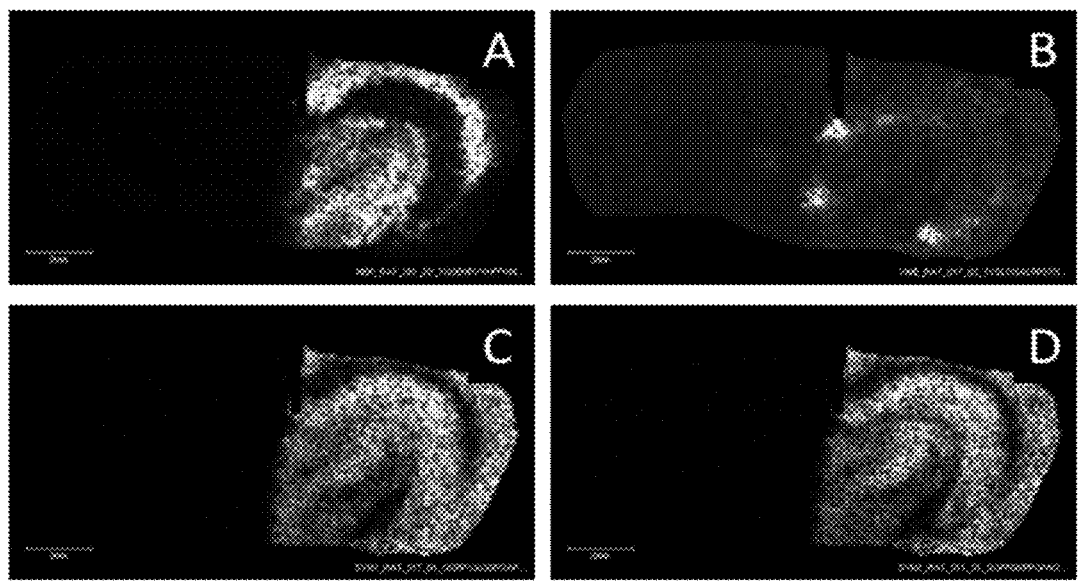
FIG. 4 shows the distribution of individual monoisotopic masses of selected trypsin digest peptides in the rat's brain of FIG. 3. According to the invention, the digest peptides were assigned to the following proteins: A) Myelin Basic Protein, B) Vimentin, C) and D) Synapsin-1. The two digest peptides of Synapsin-1 obviously correlate in their distribution, while the distributions of the three proteins in the rat's brain differ greatly from each other.

The thin section of the rat's brain from FIG. 3 was processed in this way. Its left side was covered during the nebulization with trypsin in order to digest only the right side for the purpose of comparison. After digestion and application of the matrix layer, a mass spectrometric image was acquired with the raster scanning method, image point by image point, of which FIG. 4 shows the distribution of individual monoisotopic masses.

The second tissue sample, whose digest peptides are to be measured in step (c), should be a tissue section which is as comparable as possible, with the same proportions of all tissue types. It is advantageous, if the second thin tissue section is from a nearby cut, if possible even an adjacent thin section, and it is essential that the enzymatic digestion is done in the same way as that of the first thin tissue section. It is highly advantageous, for example, to apply the same spray and incubation processes to two adjacent thin tissue sections side by side in order to achieve digest peptide distributions which are as similar as possible. After the digestion process, all the digest peptides of this second tissue sample are extracted together and separated by liquid chromatography or capillary electrophoresis into fractions. The fractions are analyzed in a tandem mass spectrometer by acquisition of mass spectra and daughter ion mass spectra. Parent ions are selected from the mass spectra, and in subsequent spectrum acquisitions the parent ions are fragmented into daughter ions by usual methods such as decomposition of metastable ions, collisions with collision gas molecules, or electron transfer by negative reactant ions, for example. Daughter ion mass spectra of all the digest peptides are acquired, where possible. It is possible to use many types of mass spectrometer and many different ionization and fragmentation methods, although MALDI ionization is preferably used in order to achieve a high degree of comparability between the peptide ionization in the mass spectra of the thin-section image and the peptide ionization of the extracted digest peptides.

A particularly elegant method for these measurements in step (c) uses liquid chromatography to separate the digest peptides extracted from the second tissue sample, and applies separated fractions of the eluate together with the matrix substance as individual samples on one or more MALDI sample support plates. Between 384 and 1536 samples are typically produced in this way from one tissue section. Commercially manufactured pipetting robots are available for this task, which are coupled with liquid chromatographs and automatically coat the sample support plate. It is then possible to automatically measure the mass spectra of the digest peptides and their daughter ion mass spectra from the samples on the sample support in a MALDI time-of-flight mass spectrometer equipped for measuring daughter ion spectra with corresponding control programs. Unlimited time (until all the sample is used up) is then available, in principle, for the measurement of the samples, which can each contain several digest peptides. The method is described in document U.S. Pat. No. 7,070,949 B2 (D. Suckau et al.; 2001; equivalent documents are GB 2 387 653 B and DE 101 58 860 B4) in detail and has become known under the abbreviated name "LC-MALDI".

Figure 1:
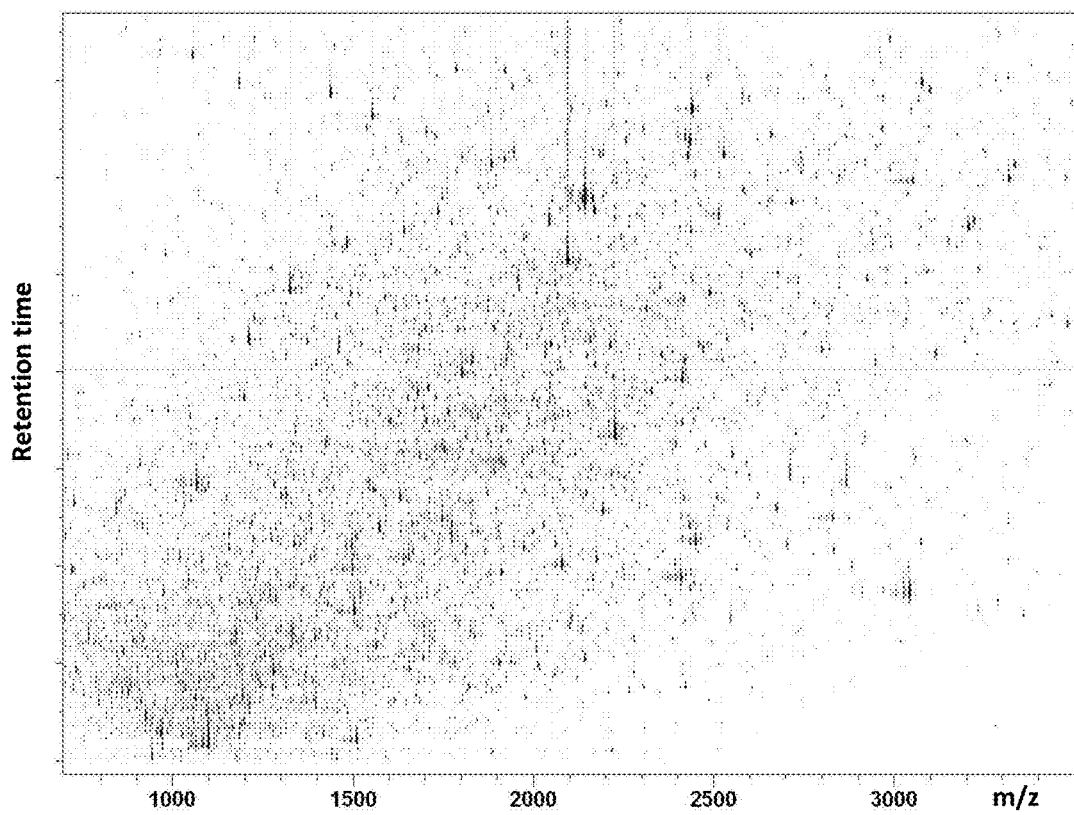
FIG. 1 depicts a mass chromatogram of the digest peptides which have been obtained from trypsin digestion of a thin tissue section of a rat's brain and acquired with the LC-MALDI method. The retention time of the peptides is shown as a function of their molecular weight in atomic mass units. Intense signals in the spectra of the individual time fractions are shown here in black, less intense ones in gray. Daughter ion mass spectra can be acquired for most of the digest peptides. A daughter ion analysis can identify around 2,000 to 20,000 digest peptides from such data sets and assign them to hundreds of proteins.
Figure 2:
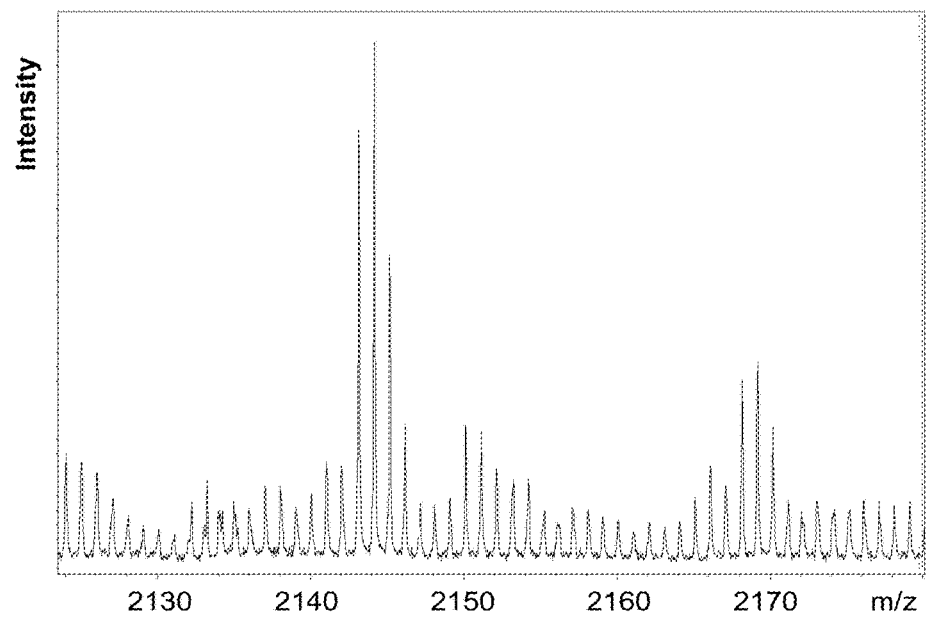
FIG. 2 depicts a small section of a mass spectrum which is the basis of the mass chromatogram of FIG. 1.

FIG. 1 shows a so-called "mass chromatogram" which was acquired with this LC-MALDI method. It depicts a mass spectrum for each retention time, where the intensities of the signals in the mass spectra are shown on a gray scale. Each gray-black dot in this mass chromatogram corresponds to a digest peptide. In the course of this method, a daughter ion mass spectrum is acquired for each digest peptide, and these spectra are used to then identify the digest peptides.

The two mass spectrometric acquisition processes of steps (b) and (c) take hours or even days, depending on the size of the thin section, the width of the scanning raster, the duration of the chromatographic separation and the number of chromatographic fractions. In commercially produced mass spectrometers they run more or less automatically and result in data volumes with magnitudes of gigabytes to terabytes in each case. The data from the LC-MALDI measurement in step (c) can be used to determine the proteins involved, as described in the cited document DE 101 58 860 B4, basically by comparison with spectra derived from spectral libraries or protein databases which are accessible in the internet. The database will be filtered so that only proteins of the relevant species (possibly genus or family) from which the thin section originates are taken into account. Depending on the differentiation of the tissue, up to 1,000 proteins, typically more than 200 different proteins, with several thousand digest peptides are identified for a thin tissue section.

It is now possible to assign the proteins in this list to the mass spectrometric image. Since, in the mass spectra of the image, each digest peptide is only characterized with its monoisotopic mass and not by additional daughter ion spectra, the procedure is simply that, in a first approximation, all proteins are assigned which have a digest peptide of the same monoisotopic mass within the measurement error range. Experience shows that the number of digest peptides in the list for identified proteins is roughly in the same order of magnitude as those of the mass spectra of the thin-section image. This means that, statistically, the assignment results in many unequivocal assignments; however, it is often necessary to preliminarily assign two, three or even more proteins to a digest peptide of the mass image, resulting in relatively many ambiguities. As will be explained below in some detail, the number of these ambiguities can be strongly decreased by intelligent filtering, confirmation and validation methods, especially by checking visually or by computing the correlation of the mass-selective images of those peptides which belong to the same protein, or, as a last measure, by obtaining a daughter ion mass spectrum from an ambiguously assigned peptide on the first tissue section used for imaging, as bad as this daughter ion mass spectrum may be.

There are several intelligent filtering methods in order to reduce the number of ambiguities. The list of the proteins with their digest peptides which was created in step (d) can be reduced before the assignments are made. Firstly, it is advisable to remove from this list all digest peptides whose monoisotopic masses are found at too low a percentage in the totality of all mass spectra of the mass spectrometric image. There is a high probability that these signals are only noise, at least if they do not form two-dimensionally or three-dimensionally connected regions. Experience has shown that a good threshold is around one percent. Secondly, all digest peptides whose abundances differ greatly from that of the other digest peptides of a given protein in the mass spectra of the thin-section image can be removed. This particularly applies when the relative abundances of the digest peptides in the mass spectra of the thin-section images which may belong to one protein essentially do not agree with those of the LC-MALDI measurements. Thirdly, digest peptides which occur too infrequently can also be removed if they are not significantly above the background noise. Furthermore, all those digest peptides can be removed whose monoisotopic mass occurs simultaneously within the measurement error range in too many proteins, for example more than ten times, because a correct assignment then becomes an improbable coincidence. Only after the list has been reduced by these filtering methods, the proteins in this reduced list are assigned to the digest peptides in the mass spectra of the mass spectrometric image of the thin tissue section, which eliminates many of the ambiguities, which would appear by using unfiltered lists.

Of great importance for avoiding assignment ambiguities is the measuring accuracy for the mass determination of the digest peptides in the image. The more accurately the masses can be determined, the lower will be the number of alternative peptides and proteins which are possible for a monoisotopic mass in the mass spectrum of an image point of the thin section within the measurement error range. Every increase in mass accuracy in the acquisition of the mass spectrometric image of the thin section is advantageous, whether it is achieved through internal recalibration of the mass spectra or by mass spectrometers with analyzers which operate more accurately, such as orthogonal time-of-flight mass spectrometers or Fourier transform mass spectrometers. The monoisotopic masses of the digest peptides of the proteins which have been determined in the steps (c) and (d) by the use of LC-MALDI can, in contrast, be determined accurately from the known molecular formulas.

For further processing, it is expedient to create a second type of list: a list of the assignments which comprises all the peptides with their monoisotopic masses for every protein which is assigned to a digest peptide of a mass spectrum of the image. This assignment list can also contain further characteristics for every digest peptide, such as the relative intensity from the LC-MALDI measurements and the multiplicity of the assignment, which states how many proteins have been assigned to a digest peptide of these monoisotopic masses in each case. This assignment list can be ordered according to different aspects.

If, after the assignment, one looks at the mass-selective images of all the assigned digest peptides for a selected protein one after the other or next to each other, one finds that most of the distribution images correlate very well with each other, i.e. they show the same, often very characteristic distribution of the digest peptides. But it also happens that one or two digest peptides of this protein exhibit distributions which do not agree at all with those of the other digest peptides. If these assignments are ambiguous, i.e. if several proteins are assigned, these digest peptides do not, in all probability, belong to the protein considered; this assignment should therefore be removed. If, on the other hand, the assignment is unique, it must belong to another protein, but it may be a special form of this protein, a posttranslational modification (PTM), or a breakdown product, not identified as such in the protein list.

The invention therefore further proposes that the mass-selective images of the digest peptides of each protein be visually or computationally correlated with each other, and that digest peptides of non-correlating distributions be removed from the list or marked separately for a more detailed investigation. The digest peptides of non-correlating selective mass images may correlate with the digest images of other proteins and may then be possibly assigned to them.

The correlation of the mass-selective images of two digest peptides of one protein can be carried out visually or computationally. The visual correlation has already been described. The computational correlation is in principle quite simple. The percentage of the image points is determined where either both images contain no signals of these digest peptides or both images contain positive signals of the digest peptides. If this percentage of matching occurrence is high, there is a positive correlation. The local noise can strongly interfere with the correlation, however. To determine the correlation, it is therefore favorable to take the local noise in the mass-selective images into account, for example by subjecting each mass-selective image to an edge-preserving smoothing process before the correlation. Of course, other correlation methods can also be used here, for example those which also take into account the intensities of the signals, or those which do not simply correlate image point by image point, but include adjacent image points in order to take account of the image noise. There are many mathematical correlation methods, including those which are already used in digital image processing.

After all the proteins have been assigned to the masses of the digest peptides of the thin tissue section image, digest peptides with unusual spatial distributions may remain to which no protein has been assigned. Since it is extraordinarily unlikely that the thin-section image will reveal digest peptides of proteins which have not been found in the LC-MALDI method, a correlation analysis can be used to search for proteins which have the same distribution. If one finds such proteins, the digest peptides may also stem from derivatives with unusual posttranslational modifications which cannot be found in the protein databases. There is a high probability that these modifications are to be found at the locations of these digest peptides. These digest peptides can then also be marked in a special way in order to subject them to further investigations.

Such further investigations could entail the acquisition of daughter ion spectra of the relevant digest peptides at image points concerned, which may be obtained also in other cases of doubtful assignments. If such daughter ion spectra of individual image points have to be acquired for the purpose of verification, it may be possible to increase the amount of substance available for these daughter ion spectra by enlarging the laser spot on the thin section or by small movements of the laser spot into a surrounding area. Even if the qualities of these daughter ion mass spectra are rather bad, showing only the positions of two or three amino acids, they may well serve for the purpose of confirmation or exclusion of an assumed peptide structure.

After reducing the ambiguities as much as possible, the mass-selective images of all the digest peptides of a protein which correlate well with each other can be summarized into an image of the protein. These protein images can be processed further; it is, for example, possible to smooth them with an edge-preserving smoothing method. Eventually a library of the protein-specific images in this thin section is produced which shows very clearly the distribution of the individual proteins. This library can form the basis for further investigations, for example in order to find out which proteins always occur together and are therefore possible interaction partners, or which proteins never occur together. The joint presence of proteins and pharmaceutical products may also be interesting. Of particular interest are those proteins which make it possible to detect diseased tissue parts or distinguish them from each other; they could be considered to be biomarkers.

Since the measurements of the digest peptides of a tissue in step (c) and the creation of the lists of proteins and digest peptides in step (d) take a long time, it is a favorable procedure to carry out these steps only once and to use the protein lists for the assignment to the mass spectra of several similar thin-section images. Although the number of ambiguities may increase, it is thus possible to create a library of such protein lists for different types of tissue sections and to use the protein lists repeatedly for different types of mass spectrometric thin-section images. In general, these protein lists contain far more proteins than can be assigned to the mass spectra of the thin-section images.

In presently available commercial mass spectrometers, sections of the overall method like steps (b) and (c) can already run automatically. All five steps (a) to (e) comprise methods which can be easily automated, from the spray method for enzymes or matrix substances, and the preparation methods for LC-MALDI, through to the mass spectrometric acquisition and data evaluation methods. Software for the control of these methods is commercially supplied with the mass spectrometers and the other equipment required. Such equipment includes spray equipment for protease and matrix solutions and incubators, and liquid chromatographs with pipetting devices for the preparation of MALDI samples on support plates.

For a medium-sized thin section measuring one to two square centimeters, with selection of a medium-fine raster scan with a width of 50 micrometers, the mass spectrometers commercially available today can produce a library with several hundred protein images of a thin section with the aid of this invention, and with relatively little manual effort, in one day, or a few days at most.

Although primarily developed for thin sections of deep-frozen tissue, the method can also be applied to thin sections of chemically stabilized tissue. Samples of tissues from clinical archives, partially very old, stabilized by FFPE or similar methods, become accessible by this new type of molecular imaging analysis.

The method also allows entering new fields of application of imaging mass spectrometry, for instance, focused on glycoproteins. The basic method for protein identification in peptide digestion images can be projected on a one-to-one basis onto the glycan group identification in glycoprotein digestion product images. Many of the proteins of a cell are glycoproteins. The digestion of the glycoproteins of two tissue sections may be performed in a step (a1) by enzymes called glycosidases. For instance, glycosidase F separates the N-linked glycans from the glycoproteins and the glycans become, directly or after further chemical modifications, accessible to MALDI imaging. N-linked glycans are linked to asparagine residues within the protein chain of amino acids; they cover molecular masses in the range of 1,000 to 5,000 atomic mass units. Glycans can also be chemically modified such that they can be easily ionized by MALDI; this may be an additional step after step (a1). In step (b1), a mass spectrometric image is acquired of the glycans in the first tissue section. In step (c1) the extracted glycans of the second tissue section will be separated chromatographically, e.g. by graphitized carbon columns or by ZIC-HILC columns, and the separated fractions can be analyzed by acquisition of mass spectra and daughter ion mass spectra. For the identification of the glycans in step (d1), there are glycan structure data bases and corresponding identification computer programs available. The identified glycans can be assigned by their precise masses to the glycans in the spectra of the mass spectrometric image in a step (e1). Glycan imaging and peptide imaging may even be performed in parallel to find correlations between specific glycans and proteins. Modifications of glycoproteins are interesting biomarkers for tumors.

In general, not only proteins or glycoproteins, but several other types of biomolecules may become accessible for identification in imaging mass spectrometry, using exactly the same basic principles. The biomolecules may comprise protein-conjugates like glycoproteins, proteoglycans, or lipoproteins, but also glycolipids and other molecules not conjugated with proteins. A general method for the identification and localization of biomolecules in a histologic thin tissue section may comprise the steps:

(A) digesting enzymatically in situ the biomolecules in two thin tissue sections with the same digestion procedure;

(B) acquiring a mass spectrometric image of the biomolecule digestion products of the first thin tissue section;

(C) extracting the biomolecule digestion products of the second thin tissue section, separating the products by a separation method, and acquiring mass spectra and daughter ion mass spectra of separated fractions of the biomolecule digestion products;

(D) identifying the biomolecule digestion products of the second tissue section, comparing the mass spectra and daughter ion mass spectra from step (C) with biomolecule structure databases or spectral libraries, and creating a list of the biomolecules with their digestion products in the second tissue section; and (E) Assigning the biomolecule digestion products in the biomolecule list, on the basis of their measured or calculated masses, to the biomolecule digestion products of the same mass in the mass spectra of the mass spectrometric image of the first thin tissue section.

While the invention has been shown and described with reference to a number of embodiments thereof, it will be recognized by those skilled in the art that various changes in form and detail may be made herein without departing from the spirit and scope of the invention as defined by the appended claims.

The invention claimed is:

1. A method for the identification and localization of proteins in a first histologic thin tissue section taken from a tissue sample, comprising:
   (a) digesting enzymatically in situ the proteins in the first tissue section and the proteins in a second tissue section that is taken from the tissue sample and that has a composition similar to the first tissue section;
   (b) acquiring mass spectra for a mass spectrometric image of the first tissue section;
   (c) extracting the digest peptides of the second tissue section, separating the digest peptides by a separation method, and acquiring mass spectra and daughter ion mass spectra from the digest peptides in separated fractions;
   (d) identifying the proteins of the second tissue section by comparing the mass spectra and the daughter ion mass spectra acquired in step (c) with protein databases and spectral libraries, and creating a protein list with information on the digest peptides of the proteins; and
   (e) assigning the proteins in the protein list, on the basis of one of measured and calculated masses of the digest peptides of the proteins, to the digest peptides having a same mass in the mass spectra of the mass spectrometric image of the first tissue section.

2. The method of claim 1, wherein step (a) comprises performing an enzymatic digestion of proteins in the first and second tissue sections by repeatedly spraying the first and second tissue section with droplets of a solution of an enzyme with interspersed drying intervals, and then incubating substantially dried first and second tissue sections at a predetermined humidity level and at a predetermined digestion temperature for a predetermined time.

3. The method of claim 1, wherein step (b) comprises acquiring the mass spectrometric image by applying a matrix substance layer to the first tissue section and performing ionization by matrix-assisted laser desorption.

4. The method of claim 1, wherein the second tissue section is taken from the tissue sample at a location near the location from which the first tissue section was taken and step (a) comprises performing enzymatic digestion on the second tissue section and the first tissue section in identical manners.

5. The method of claim 4, wherein the first tissue section and the second tissue section are taken as adjacent sections of the tissue sample.

6. The method of claim 1, wherein step (c) comprises separating the digest peptides by liquid chromatography or capillary electrophoresis.

7. The method of claim 1, wherein step (c) comprises producing daughter ions by fragmenting selected parent ions by one of decomposition of metastable ions, spontaneous decomposition, collisions with molecules of a collision gas and electron transfer from negative reactant ions.

8. The method of claim 1, wherein step (c) comprises separating digest peptides by liquid chromatography to create eluate fractions, preparing the eluate fractions together with a matrix substance as individual samples on at least one MALDI sample support plate, and measuring daughter ion spectra from the samples in a MALDI mass spectrometer equipped for measurement of daughter ion spectra.

9. The method of claim 1, wherein step (e) comprises assigning proteins in the protein list created in step (d) to the mass spectrometric image so that all proteins in the protein list, which possess (within a predetermined error or tolerance range) a digest peptide of the same monoisotopic mass as a digest peptide in the mass spectra of the mass spectrometric image of the first tissue section, are assigned to this digest peptide.

10. The method of claim 1, wherein step (d) further comprises removing from the protein list all digest peptides which fulfill at least one of the following:
   (i) in terms of their mass, are found with a percentage below a predetermined threshold in the totality of the mass spectra of the mass spectrometric image,
   (ii) in relation to other digest peptides, have abundance ratios in the mass spectra of the mass spectrometric image which differ from abundance ratios in the mass spectra acquired in step (c), and
   (iii) occur in more than a predetermined percentage of proteins in the protein list.

11. The method of claim 1, wherein step (e) further comprises, for each protein, correlating mass-selective images of the digest peptides by one of visual and computational means, and removing an assignment of a protein to a digest peptide whose correlation with mass-selective images of other digest peptides of this protein is below a predetermined threshold.

12. The method of claim 11, wherein step (e) further comprises summarizing into an image of a protein, images of all digest peptides of that protein which have correlations above a predetermined threshold.

13. The method of claim 1, further comprising using the protein list obtained in step (d) to assign proteins in the protein list to the digest peptides of the same mass in mass spectra of mass spectrometric images of tissue sections taken from the tissue sample in addition to the second tissue section.

14. The method of claim 1, further comprising acquiring a daughter ion mass spectrum from a position in the first tissue section when the digest peptides in the mass spectra of the mass spectrometric image have no assignments or ambiguous assignments.

15. The method of claim 1, wherein the thin tissue section has been chemically stabilized.

16. A method for the identification and localization of glycan groups on glycoproteins in a first histologic thin tissue section taken from a tissue sample, comprising:
   (a) digesting enzymatically in situ the glycoproteins and separating the glycan groups from the glycoproteins in the first tissue section and in a second tissue section that is taken from the tissue sample and that has a composition similar to the first tissue section;
   (b) acquiring a mass spectrometric image of the glycan groups of the first tissue section;
   (c) extracting the separated glycan groups of the second tissue section in separated factions, and acquiring mass spectra and daughter ion mass spectra of the separated fractions of the glycan groups;
   (d) identifying the glycan groups of the second tissue section by comparing the mass spectra and the daughter ion mass spectra acquired in step (c) with glycan structure databases or spectral libraries, and creating a glycan group list with information on the separated glycan groups from the digested glycoproteins; and
   (e) assigning the glycan groups in the glycan group list, on the basis of one of measured or calculated masses of the separated glycan groups, to the glycan groups having the same mass in mass spectra of the mass spectrometric image of the first tissue section in step (b).

17. A method for the identification and localization of biomolecules in a first histologic thin tissue section taken from a tissue sample, comprising:
   (a) enzymatically digesting in situ the biomolecules in a first tissue section and the biomolecules in a second tissue section that is taken from the tissue sample and that has a composition similar to the first tissue section;
   (b) acquiring mass spectra for a mass spectrometric image of biomolecule digestion products in the first tissue section;
   (c) extracting biomolecule digestion products from the second tissue section, separating the extracted digestion products by a separation method, and acquiring mass spectra and daughter ion mass spectra of separated fractions of the biomolecule digestion products;
   (d) identifying biomolecules of the second tissue section by comparing the mass spectra and the daughter ion mass spectra acquired in step (c) with biomolecule structure databases or spectral libraries, and creating a biomolecule list with the digestion products; and
   (e) assigning the biomolecules in the biomolecule list, on the basis of one of measured and calculated masses of the biomolecule digestion products of the biomolecules, to the biomolecule digestion products having a same mass as digestion products in the mass spectra of the mass spectrometric image of the first tissue section.

* * * * *